US012799451B2

(12) United States Patent
Hamrick

(10) Patent No.: US 12,799,451 B2
(45) **Date of Patent: *Nov. 17, 2026**

(54) CONTAMINATION CONTROL WHEN GROWING YEASTS

(71) Applicant: Edward Brian Hamrick, Sunny Isles Beach, FL (US)

(72) Inventor: Edward Brian Hamrick, Sunny Isles Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/202,839

(22) Filed: May 8, 2025

(65) Prior Publication Data

US 2025/0270497 A1 Aug. 28, 2025

Related U.S. Application Data

(63) Continuation-in-part of application No. 18/532,043, filed on Dec. 7, 2023, now Pat. No. 12,297,423.

(60) Provisional application No. 63/534,123, filed on Aug. 23, 2023.

(51) Int. Cl.

| | |
|---|---|
| ***C12N 1/16*** | (2026.01) |
| ***A23K 10/16*** | (2016.01) |
| ***C12M 1/02*** | (2006.01) |
| ***C12M 1/12*** | (2006.01) |
| ***C12M 1/34*** | (2006.01) |

(52) U.S. Cl.
CPC ................ *C12N 1/16* (2013.01); *A23K 10/16* (2016.05); *C12M 37/00* (2013.01); *C12M 41/18* (2013.01); *C12M 41/34* (2013.01)

(58) Field of Classification Search
CPC ................................. C12N 1/16; C12M 37/00
See application file for complete search history.

(56) References Cited

U.S. PATENT DOCUMENTS

| | | | | |
|---|---|---|---|---|
| 6,197,573 B1 * | 3/2001 | Suryanarayan | C12M 41/22 | 435/291.3 |
| 6,252,016 B1 * | 6/2001 | Wu | B01J 19/249 | 422/138 |
| 2014/0024064 A1 * | 1/2014 | Burlew | C11B 1/025 | 435/157 |

OTHER PUBLICATIONS

Thomas et al., Applied and Environmental Microbiology, 1990, 56(7): 2046-2050.*
Kakimoto et al., Appl Microbiol Biotechnol, 1990, 32:538-543.*
Verbelen et al., Appl Microbiol Biotechnol, 2009, 82:1143-1156.*
Milne et al., Metab. Eng., 2015, 30:130-140 (Year: 2015).*
Eitinger et al., J. Biol. Chem., 2000, 275(24): 18029-18033 (Year: 2000).*
Hensing et al., Appl. Microbiol. Biotechnol, 1995, 43:58-64 (Year: 1995).*
Wongsurakul et al., "Comprehensive review on potential contamination in fuel ethanol production with proposed specific guideline criteria", Energies 2022, 15, 2986.

* cited by examiner

*Primary Examiner* — Manjunath N Rao
*Assistant Examiner* — Qing Xu
(74) *Attorney, Agent, or Firm* — O'Connor & Company; Ryan P. O'Connor

(57) ABSTRACT

A method for contamination control when growing yeasts is provided. Bacterial contamination is controlled by using urea as the primary nitrogen source while simultaneously limiting the amount of nickel available to contaminating bacteria. Bacteria require nickel as a cofactor for urease enzymes in order to use urea for growth while yeasts do not require nickel as a cofactor for any enzymes. Nickel is limited by using metals in heat exchangers that do not leach nickel. Ethyl carbamate is limited by using a carbon/nitrogen ratio that consumes all urea during fermentation. After fermentation completes, yeast is recycled using centrifugation, enabling use of high concentrations of yeast to reduce fermentation time from 48 hours to 12 hours and to eliminate bacterial contamination from growth on free amino nitrogen.

19 Claims, No Drawings

CONTAMINATION CONTROL WHEN GROWING YEASTS

PRIORITY DATA

This patent application is a continuation-in-part application of U.S. Pat. No. 12,297,423, issued on May 13, 2025, which claims priority to U.S. Provisional Patent App. No. 63/534,123, filed on Aug. 23, 2023, each of which is hereby incorporated by reference herein for all purposes.

FIELD OF THE INVENTION

The present invention pertains to growth of microorganisms. More specifically, this invention pertains to contamination control when growing yeasts.

BACKGROUND OF THE INVENTION

Industrial-scale growth of yeasts is commonly used to make single cell protein (SCP) or coproducts such as ethanol. This growth is herein referred to as 'fermentation' and uses a 'fermenter' to grow these yeasts, even when there are no coproducts such as ethanol, and even when the process is either aerobic or anaerobic.

One problem with growing yeasts at an industrial scale, such as in fermenters with a volume of more than 100 $m^3$, is contamination by other microorganisms.

For instance, industrial-scale fermenters using *Saccharomyces cerevisiae* to produce ethanol from sugars are often contaminated by lactic acid bacteria such as *Lactobacillus fermentum* or by wild yeasts such as Dekkera bruxellensis and its anamorph Brettanomyces bruxellensis. Contamination is especially common when yeast is recycled. This contamination is described in Bassi, Ana Paula Guarnieri, et al., "Interaction of *Saccharomyces cerevisiae-Lactobacillus fermentum*-Dekkera bruxellensis and feedstock on fuel ethanol fermentation", Antonie Van Leeuwenhoek 111 (2018): 1661-1672, which is hereby incorporated by reference.

Contamination occurs when the growth rate of an undesired microorganism is higher than the growth rate of a desired microorganism. For instance, the doubling time of most lactic acid bacteria is about 0.5 hours and the doubling time of many yeasts is about 1.5 hours. This means that over a 24-hour period, a single bacterial cell of lactic acid bacteria grows to $2^{24/0.5}$ or $3\times10^{14}$ cells, whereas a single yeast cell grows to $2^{24/1.5}$ or $7\times10^{4}$ cells. Reducing the growth rate of lactic acid bacteria to slightly less than that of a yeast (increasing the doubling time to just a bit more than 1.5 hours) completely eliminates the problem of contamination, even over many months of continuous fermentation. Often forgotten is that increasing the growth rate of yeast (e.g., by using urea as the nitrogen source) also reduces contamination.

Contamination control is directly related to the time of fermentation and the initial concentration of undesired microorganisms and desired microorganisms, and to the growth rate of these organisms. Simple calculations show that longer fermentations have more of a problem with contamination than shorter fermentations, factoring in the different growth rates of these microorganisms.

Therefore, contamination can be controlled by a combination of reducing the fermentation time (e.g., yeast recycling when making fuel ethanol in Brazil), killing contaminating microorganisms (e.g., washing recycled yeast with sulfuric acid), or reducing the growth rate of contaminating microorganisms (e.g., with antibiotics).

Industrial-scale growth of yeasts is necessarily performed in non-aseptic conditions since industrial-scale aseptic growth is prohibitively expensive. The most common methods of contamination control in industrial-scale fermentation have been the use of sulfites ($SO_2$), antibiotics and peroxides.

Winemakers in ancient Rome burned sulfur candles in wine containers to control contamination that turned wine to vinegar, currently known to be caused by acetic acid bacteria such as *Acetobacter aceti*. Today, sulfites are often used to prevent bacterial growth in winemaking. However, sulfites cause allergic reactions in some people, and wine labels must have warnings that the wine contains sulfites.

The first successful industrial-scale fermentation of SCP was performed in Germany in the 1930s and 1940s using waste liquor from sulfite pulping. This is described in Inskeep, Gordon C., et al., "Food yeast from sulfite liquor", *Industrial & Engineering Chemistry* 43.8 (1951): 1702-1711, which is hereby incorporated by reference. Inskeep notes that "The yeast fermentation has been remarkably free from contamination. In more than 2 years of operation of the Lake States plant, production has never been interrupted because of contamination. The conditions of pH, temperature, and aeration with agitation permit the propagation of *T. utilis* at rates rapid enough to overgrow and prevent the development of foreign organisms." Inskeep also notes that "The pH of the fermentation mixture (wort) runs about 5.0." It seems that Inskeep didn't consider that residual sulfites from pulping probably caused the lack of bacterial contamination. Also, in the 1950s, allergic reactions to sulfites weren't known.

Fuel ethanol producers today often use antibiotics to control bacterial contamination in industrial-scale fermentation. However, this is expensive. Additionally, the valuable coproduct of dried distiller's grains with solubles (DDGS) is contaminated by these antibiotics which enter the food chain, leading to antibiotic-resistant bacteria which cause illnesses in people. This is described in Olendorff, Samantha A., Karolina Chmielewska, and Kevin R. Tucker, "Survey of antibiotics residues in DDGS from 14 different states by LCM", *Cereal Chemistry* 98.1 (2021): 81-88, which is hereby incorporated by reference.

Attempts have been made to control bacterial contamination using urea hydrogen peroxide and nitrogen-free peroxygen-releasing compounds. The use of urea hydrogen peroxide to control *lactobacillus* contamination is described in Narendranath, N. V., K. C. Thomas, and W. M. Ingledew, "U rea hydrogen peroxide reduces the numbers of lactobacilli, nourishes yeast, and leaves no residues in the ethanol fermentation", *Applied and Environmental microbiology* 66.10 (2000): 4187-4192, which is hereby incorporated by reference. The use of nitrogen-free peroxygen-releasing compounds to control bacterial contamination is described by Solomon in U.S. Pat. No. 8,759,051, issued on Jun. 24, 2014, which is hereby incorporated by reference. However, the use of peroxides to control bacterial contamination has been shown to be uneconomical and is not widely used today in industrial-scale fermentation processes.

Four microorganisms have been used for more than 30 years to make SCP that can be safely consumed by people and fed to animals. A yeast that has been used to make SCP from hexose sugars and from hydrolyzed starch for more than 100 years is *Saccharomyces cerevisiae*, more commonly known as baker's yeast, brewer's yeast or just yeast. A yeast that has been used to make SCP from hydrolyzed starch, hexose sugars and pentose sugars for more than 80 years is *Cyberlindnera jadinii*, more commonly known as

*Candida utilis* or Torula. A yeast that has been used to make SCP from hydrolyzed starch, hexose sugars, lactose and galacturonic acid for more than 50 years is *Kluyveromyces marxianus*, also known as *Candida kefyr* and *Kluyveromyces lactis*. A yeast that has been used to make SCP from lipids (oils) for more than 50 years is *Yarrowia lipolytica*.

All four of these yeasts have been recognized in the United States as Generally Recognized as Safe (GRAS) and have received similar approvals in many other countries, including Canada, Europe, Australia, Brazil, Russia, India, and China. All have been extensively tested and shown to be safe in animal feed (especially fish and chicken) and for human consumption. *Candida utilis* (Torula) is even commonly used today as a flavor enhancer—it has an umami (meaty) flavor and tastes good.

Bacterial contamination is often the biggest technical problem when using yeasts in industrial-scale fermentation to produce ethanol, single-cell protein and Omega-3 lipids. The need exists for industrial-scale contamination control without using sulfites, antibiotics, acid washes, or peroxides when producing fuel ethanol and when growing yeasts for SCP.

In the United States, production of fuel ethanol for blending with gasoline started in the 1980's and took off after 2000. The Energy Tax Act of 1978 introduced a partial exemption from the federal gasoline excise tax for fuels blended with ethanol. Blending mandates for ethanol in gasoline in the United States began with the Energy Policy Act of 2005. These government policies and the low-cost production of corn has resulted in United States becoming the largest producer of fuel ethanol in the world, with Brazil a close second.

Brazil has the lowest cost of production of fuel ethanol in the world and has refined the fermentation process to produce ethanol from sugarcane juice in 12 hour cycles by using recycled yeast. The dry-grind corn ethanol process in the US ferments hydrolyzed ground corn to ethanol in 48 to 72 hours using Simultaneous Saccharification and Fermentation (SSF) at 32° C., requiring significantly more capital for fermentation tanks compared to Brazilian fermenters and resulting in higher cost of ethanol production.

From about 1990 to 2017, glucoamylase enzymes such as Novozymes' AMG product line were only stable for about an hour at temperatures above 40° C. This made SSF the most economical process of hydrolyzing dextrins to glucose, so most current U.S. corn ethanol plants were built to use SSF, hydrolyzing dextrins to glucose at the same time as fermenting glucose to ethanol with yeast. This worked well but is less efficient than the Brazilian process of using yeast recycling.

Starting in about 2017, companies began producing glucoamylase enzymes that are stable at temperatures up to 65° C., such as the Novozymes Spirizyme® product line. This makes it up to 8 times faster to produce glucose from dextrins at 65 C compared to the older generation of enzymes at 32° C.

These newer glucoamylase enzymes make Separate Hydrolysis and Fermentation (SHF) more efficient than SSF, since the saccharification is sped up at higher temperatures and since saccharification and fermentation can be overlapped in batch processes. Fermentation can only be sped up if the Brazilian technique of yeast recycling can be performed, especially if acid washing of yeast isn't done. However, if acid washing of recycled yeast is done, the wash water has to be introduced into the distillation column, making recovery of proteins and lipids from stillage impractical and making using stillage as backset impractical. If acid washing of recycled yeast isn't done, then bacterial contamination isn't controlled.

A key part of the economics of producing fuel ethanol from corn is that the coproducts, mainly Distillers Dried Grains and Solubles (DDGS) are a valuable product sold as animal feed, supplementing the revenues from the fuel ethanol. These coproducts are currently produced by centrifuging the stillage after distillation to recover 70% of the protein in the corn and 60% of the corn oil, then concentrating the thin stillage with evaporation to recover the remaining 30% of protein and 40% of the corn oil. Protein and oils are what make DDGS animal feed valuable.

However, producing DDGS this way makes it difficult to separate yeast by differential centrifugation from corn solids after fermentation and before distillation, since yeast doesn't survive distillation. A complicated two-stage centrifugation is needed to do this, described in U.S. Pat. No. 12,297,423. Differential centrifugation is expensive and time consuming, so a method of yeast recycling is needed that uses less expensive centrifugation for yeast recycling so that fermentation time can be decreased and that allows faster saccharification of dextrins to glucose at higher temperatures.

There are two main types of crops that are used to produce ethanol, grasses in the Poaceae family with sugar rich stalks (sugarcane and sweet sorghum) and grasses in the Poaceae family with starch-rich grains (corn, wheat, rice, sorghum). Some varieties of sweet sorghum can produce both sugar and grains in the same harvest.

Sugarcane and sweet sorghum stalks need to be processed to ethanol within a few hours of harvest, making it necessary to locate the ethanol plants near where the crops are grown. The sugarcane harvest in Brazil and India lasts for about 8 months, with 4 months for plant maintenance and producing ethanol from starch. However, sometimes sugar is more valuable than ethanol, leaving these ethanol plants partially idle. Sugarcane and sweet sorghum need different climates for optimal growth, so they can seldom be produced within a few hours of the same ethanol plant, making it impractical for the same ethanol plant to make ethanol from both.

Sweet sorghum has a harvest season, even with staggered planting, of 4 months at most. This makes it uneconomical to build ethanol plants that can only make ethanol from sweet sorghum juice, since they would then be left idle for 8 months each year. This could be a valuable crop if a sweet sorghum ethanol plant could also be used to make ethanol from grain during these 8 months, since grain can be cost-effectively transported by train and stored year-round after drying to 15% moisture.

The U.S., Brazil, Russia, India, and China all have huge areas of agricultural land suitable for growing sweet sorghum. The U.S. Southeast (e.g., North Carolina and Georgia) and the U.S. Sorghum Belt (e.g., Kansas and Texas) are prime locations for sweet sorghum ethanol production, with harvest seasons lasting 3-4 months, peaking in late summer to fall. Northeast and Central-West Brazil stand out as the best areas to grow sweet sorghum due to their climate, scale, and existing ethanol infrastructure. Sweet sorghum is primarily grown in Russia's southern regions, where hotter and drier conditions mimic the crop's preferred environment. Key areas include Saratov Oblast, Volgograd Oblast, Rostov Oblast, Orenburg Oblast, and Stavropol Krai. The best areas for growing sweet sorghum for ethanol in India include Maharashtra, Tamil Nadu, Gujarat, Andhra Pradesh/Telangana, Uttar Pradesh, and Karnataka, leveraging their semi-arid to sub-tropical climates and agricultural infrastructure. China has approximately 32-49 million hectares of marginal land suitable for sweet sorghum, particularly in saline-alkali, barren, or underutilized areas, reducing competition with food crops. The harvest season per crop cycle lasts about 2-4 weeks, with a total potential annual harvest period of 3-4 months if multiple seasons are utilized.

Sweet sorghum can produce more sugar per hectare than any other crop, but since the harvest season is so short, it's not cost-effective to build a plant to make ethanol or single-cell protein from sweet sorghum because this plant would lie idle for 8 months per year. This is why few places in the world produce ethanol or single-cell protein from sweet sorghum. In addition, it's not possible to produce crystallized sucrose from sweet sorghum because the stalks contain too much invert sugar (glucose and fructose). In countries that don't make fuel ethanol (like Russia), sweet sorghum isn't a valuable crop because it can't be used to make crystallize sucrose (table sugar).

The top 4 ethanol-producing countries are the USA (57.7 billion liters, 97% from corn), Brazil (27.6 billion liters, 95% from sugarcane, 5% from corn), India (4.5 billion liters, 80% from sugarcane, 10% from corn, 10% from wheat), and China (3.2 billion liters, 70% from corn, 10% from sugarcane, 10% from wheat, 10% from sugar beet).

If it were possible to cost-effectively build flex plants that could make ethanol from both sugar-rich stalks and from grain, then making ethanol from sweet sorghum and grain would be very profitable in the U.S., Brazil, India, and China. If it were possible to cost-effectively modify existing sugarcane ethanol plants to produce ethanol from grain, this would increase the profitability of existing sugarcane ethanol plants in Brazil and India.

If it were possible to cost-effectively build flex plants that could make single-cell protein from both sugar-rich stalks and from grain, then making single-cell protein from sweet sorghum and grain would be very profitable in the U.S., Brazil, Russia, India, and China. If it were possible to cost-effectively modify existing sugarcane ethanol plants to produce single-cell protein from both sugarcane juice and grain, this would increase the profitability of existing sugarcane ethanol plants in Brazil and India.

SUMMARY OF THE INVENTION

Some variations of the invention provide a method for contamination control when growing yeasts, the method comprising growing yeasts for a fermentation time at a starting pH in a fermentation broth comprising a sugar solution, free amino nitrogen, urea, a mineral source, yeasts, and contaminating bacteria, wherein the amount of nickel in the fermentation broth is less than 1 mg/kg during the entirety of the fermentation time, wherein the urea is introduced to the fermentation broth via fed-batch feeding over time, with the fed-batch feeding commencing after the yeasts consume more than 90% of the free amino nitrogen in the fermentation broth, then controlling the fed-batch feeding such that the pH of the fermentation broth does not rise, due to addition of the urea, during the entirety of the fermentation time, wherein the sugar solution contains sugars selected from the group consisting of sucrose, glucose, fructose, mannose, galactose, lactose, xylose, maltose, and combinations thereof, wherein the sugar solution has a starting concentration of sugars greater than 50 g/L, wherein the free amino nitrogen has a starting concentration between 10 mg/L and 400 mg/L of nitrogen, wherein the yeasts have a starting concentration of more than 50 g/L wet weight, wherein the contaminating bacteria have a starting concentration of less than $10^7$ CFU/mL, wherein the fermentation time is between 2 hours and 18 hours, during which the yeasts grow by metabolizing the sugars, the free amino nitrogen, the urea, and the mineral source in the fermentation broth, wherein the yeasts produce metabolites in the fermentation broth, and wherein the metabolites are selected from the group consisting of ethanol, carbon dioxide, glycerol, acetaldehyde, and combinations thereof, wherein a portion of the yeasts is separated from the fermentation broth after the fermentation time to produce recycled yeasts, and wherein the recycled yeasts are not washed with acid, a fraction of the recycled yeasts is re-used in subsequent cycles as the yeasts, and the remaining fraction of the recycled yeasts is used as a yeast cream co-product.

In some embodiments, the sugar solution is produced from grain by first grinding the grain to produce a ground grain, forming a slurry of the ground grain and alpha-amylase enzymes and liquifying the slurry to a dextrin solution containing dextrin at a temperature above 80° C., saccharifying more than 95% of the dextrin to provide a saccharified solution using glucoamylase enzymes at a temperature between 50° C. and 65° C., and centrifuging the saccharified solution to produce a supernatant of the sugar solution and a co-product cake.

In some embodiments, the sugar solution is produced from solutions selected from the group consisting of sugarcane juice, clarified sugarcane juice, sugarcane molasses solution, raw sugar solution, sweet sorghum juice, clarified sweet sorghum juice, sugar beet juice, clarified sugar beet juice, sugar beet molasses solution, sucrose solution, glucose solution, fructose solution, mannose solution, galactose solution, lactose solution, xylose solution, maltose solution, and combinations thereof.

In some embodiments, the yeasts are selected from the group consisting of *Saccharomyces cerevisiae, Cyberlindnera jadinii, Kluyveromyces marxianus, Yarrowia lipolytica*, and combinations thereof.

In some embodiments, the contaminating bacteria is *Lactobacillus fermentum.*

In some embodiments, the fermentation broth contains the ethanol which is separated, using distillation, to produce a hydrous ethanol product and distillation stillage.

In some embodiments, the step of separating the recycled yeasts from the fermentation broth is selected from the group consisting of centrifugation, filtration, sedimentation, foam fractionation, and combinations thereof.

In some embodiments, the co-product cake is dried to less than 12 wt % moisture to produce a dried animal feed product.

In some embodiments, a portion of the distillation stillage is mixed with water to form the slurry, and the remainder of the distillation stillage is concentrated to produce an animal feed syrup.

In some embodiments, the grain is selected from the group consisting of corn, wheat, rice, sorghum, and combinations thereof.

In some embodiments, the fermentation broth is in operable communication with a heat exchanger, wherein the heat exchanger is a plate heat exchanger comprising titanium heat exchange plates, and wherein the titanium heat exchange plates contain less than 1 g/kg nickel.

In some embodiments, the fermentation broth is in operable communication with a heat exchanger, and wherein the heat exchanger is a plate heat exchanger comprising stainless steel grade 316 heat exchange plates.

In some embodiments, the fermentation broth is in operable communication with a heat exchanger, wherein the heat exchanger is a spiral plate heat exchanger comprising titanium heat exchange plates, and wherein the titanium heat exchange plates contain less than 1 g/kg nickel.

In some embodiments, the fermentation broth is in operable communication with a heat exchanger, and wherein the heat exchanger is a spiral plate heat exchanger comprising stainless steel grade 316 heat exchange plates.

In some embodiments, the fermentation broth is cooled by evaporative cooling.

In some embodiments, the fermentation broth is sprayed into a space to form a spray, wherein air at less than 100% relative humidity is circulated through the space, wherein the air evaporates water from the spray, and wherein the spray is returned to the fermentation broth at a reduced temperature.

In some embodiments, the ratio of the amount of the carbon source to the amount of the urea is selected such that essentially no urea remains in the fermentation broth before the hydrous ethanol product is separated from the fermentation broth by the distillation.

In some embodiments, the fermentation broth is oxygenated to maintain an oxygen level sufficient to support aerobic growth of the yeasts.

In some embodiments, the fermentation broth is oxygenated using a method selected from the group consisting of air sparging, foam fermenting, mechanical agitation, and combinations thereof.

DETAILED DESCRIPTION OF EMBODIMENTS OF THE INVENTION

The methods, processes, and systems of the present invention will be described in detail by reference to various non-limiting embodiments and figure(s).

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing parameters, conditions, results, and so forth used in the specification and claims are to be understood as being modified in all instances by the term "about." Accordingly, unless indicated to the contrary, the numbers set forth in the following specification and attached claims are approximations that may vary depending upon specific algorithms and calculations.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms, except in the case of Markush groups. Thus in some embodiments not otherwise explicitly recited, any instance of "comprising" may be replaced by "consisting of" or, alternatively, by "consisting essentially of."

No embodiments described herein shall be limited by any theory or speculation regarding reaction mechanisms, mass-transfer mechanisms, or descriptions of feedstocks or products.

The present invention is premised on a technical solution to the serious problem of bacterial contamination during yeast growth. It has been recognized by the present inventor that bacteria require nickel as a cofactor for urease enzymes in order to use urea for growth, while yeasts do not require nickel as a cofactor for any enzymes. This principle is applied by designing a fermentation system in which nickel content is minimized in the broth, while at the same time, urea is the primary nitrogen source which therefore reduces the growth rate of bacteria below the growth rate of yeast, preventing contamination.

Many bacteria, especially many which often contaminate yeast fermentations, do not contain urease enzymes and thus can't grow at all when urea is the nitrogen source. These bacteria include *Liquorilactobacillus vini* (*Lactobacillus vini*), *Lactobacillus plantarum, Lactobacillus brevis*, and *Lactobacillus casei*. However, two common contaminating bacteria which do contain urease enzymes are *Lactobacillus fermentum* and *Lactobacillus reuteri*. In this disclosure, the contamination by these organisms is controlled by reducing the amount of nickel in the fermentation broth.

Reducing the amount of nickel in the fermentation broth has been shown to significantly reduce the growth rate of bacteria in the fermentation broth. Since nickel is a catalyst for urease in bacteria, reducing the concentration of nickel by half reduces the growth of bacteria by half when urea is the primary nitrogen source.

An additional contributor to contamination control is simply using urea as the primary nitrogen source. *Lactobacillus fermentum* grows slower on urea than ammonium. This is described in Gao, X., S. Y. Qiao, and W. Q. Lu., "Determination of an economical medium for growth of *Lactobacillus fermentum* using response surface methodology", *Letters in applied microbiology* 49.5 (2009): 556-561, which is hereby incorporated by reference. M any yeasts, such as *Saccharomyces cerevisiae*, grow faster on urea than other nitrogen sources. This is described in Jones, Alison M., and W. M. Ingledew., "Fuel alcohol production: optimization of temperature for efficient very-high-gravity fermentation", *Applied and environmental microbiology* 60.3 (1994): 1048-1051, which is hereby incorporated by reference.

A complication when using urea with yeasts is that when there is too much urea inside yeast cells, they will excrete ammonium to relieve ammonium toxicity, and bacteria grow well on ammonium. When the concentration of urea is less than 0.25 mM, the urea enters the yeast cell by an inducible urea permease and above 0.5 mM, the urea enters the yeast cell by facilitated diffusion. This is described in Yang, Xinchao, et al., "Comparisons of urea or ammonium on growth and fermentative metabolism of *Saccharomyces cerevisiae* in ethanol fermentation", *World Journal of Microbiology and Biotechnology* 37.6 (2021): 98, which is hereby incorporated by reference. If this diffusion rate is higher than the kinetic need for nitrogen for growth, yeast cells will detoxify themselves of ammonium from urea by excreting ammonium. This is described in Prins, Rianne C., and Sonja Billerbeck., "A buffered media system for yeast batch culture growth", *BMC microbiology* 21.1 (2021): 1-9, which is hereby incorporated by reference. Prins shows that growth of yeast with urea as the primary nitrogen source leads to alkalinization at 5 mM urea (Prins, FIGS. 1A and 1B, left columns, unbuffered). Alkalinization is due to excretion of ammonia from yeasts. The present inventor has demonstrated experimentally that alkalinization is reduced by fed-batch addition of urea, keeping the concentration of urea below 1 mM-significantly reducing the growth rate of contaminating bacteria.

Hydrolysis of ground grain with alpha-amylase enzymes is typically at 90° C. and clarification of sugar cane juice, sweet sorghum juice, and sugar beet juice is typically at 80-100° C. High-temperature treatment kills most vegetative bacteria but heat-resistant spores may survive. Production of molasses also involves heat treatment. The bacterial concentration after heat treatment is in the range of $10^2$-$10^3$ CFU/mL, primarily spore-forming bacteria, and additional bacterial contamination from recycled yeast, pipes, and vessels further increases the bacterial concentration to about $10^5$ CFU/ml, mostly *Lactobacillus* species. The concentration of recycled yeast at the start of fermentation, given a wet weight of 100 g/L, is $2\times10^9$ CFU/ml, which is about 20,000 times more than the concentration of bacteria at the start of fermentation.

Some variations of the invention provide a method for contamination control when growing yeasts, the method comprising growing yeasts for a fermentation time at a starting pH in a fermentation broth comprising a sugar solution, free amino nitrogen, urea, a mineral source, yeasts, and contaminating bacteria, wherein the amount of nickel in the fermentation broth is less than 1 mg/kg during the entirety of the fermentation time, wherein the urea is introduced to the fermentation broth via fed-batch feeding over time, with the fed-batch feeding commencing after the yeasts consume more than 90% of the free amino nitrogen in the fermentation broth, then controlling the fed-batch feeding such that the pH of the fermentation broth does not rise, due to addition of the urea, during the entirety of the fermentation time, wherein the sugar solution contains sugars selected from the group consisting of sucrose, glucose, fructose, mannose, galactose, lactose, xylose, maltose, and combinations thereof, wherein the sugar solution has a starting concentration of sugars greater than 50 g/L, wherein the free amino nitrogen has a starting concentration between 10 mg/L and 400 mg/L of nitrogen, wherein the yeasts have a starting concentration of more than 50 g/L wet weight, wherein the contaminating bacteria have a starting concentration of less than $10^7$ CFU/mL, wherein the fermentation time is between 2 hours and 18 hours, during which the yeasts grow by metabolizing the sugars, the free amino nitrogen, the urea, and the mineral source in the fermentation broth, wherein the yeasts produce metabolites in the fermentation broth, and wherein the metabolites are selected from the group consisting of ethanol, carbon dioxide, glycerol, acetaldehyde, and combinations thereof, wherein a portion of the yeasts is separated from the fermentation broth after the fermentation time to produce recycled yeasts, and wherein the recycled yeasts are not washed with acid, a fraction of the recycled yeasts is re-used in subsequent cycles as the yeasts, and the remaining fraction of the recycled yeasts is used as a yeast cream co-product.

In summary, this variation of the invention provides the process of starting with a sugar solution and producing products of growing yeast, while simultaneously producing co-products like ethanol, single-cell protein, and animal feed. This process resembles the Brazilian sugarcane ethanol fermentation and distillation with yeast recycling, except that the recycled yeast isn't dosed with acid. Instead, bacterial contamination is prevented by using high concentrations of yeast to rapidly consume free amino nitrogen (FAN) and then depending on the facts that bacteria won't grow if the only nitrogen source is urea and that there's little nickel to allow bacteria to use urea as a nitrogen source. Existing Brazilian and Indian sugarcane ethanol plants can easily be modified to use this variation of the invention, thus making it cost-effective to also make grain ethanol at the same plant.

The subsequent two embodiments in this specification describe how to produce this sugar solution from grain and from sugar-rich crops. Persons skilled in the art will recognize that other embodiments may be employed to produce these sugar solutions, consistent with the principles disclosed herein. These other methods include using enzymatic hydrolysis and dilute-acid hydrolysis, and using alternate feedstocks such as lignocellulosic biomass, inulin-containing crops, starch-containing root crops, and other carbohydrate-containing materials.

The fermentation and production of co-products can proceed in parallel with producing the sugar solution, and since a factory simultaneously performs fermentation and production of co-products while producing sugar solutions for the next fermentation cycle. This enables using the fermenters, distillation columns, and centrifuges continuously year-round, making a plant more cost-effective.

When urea is the nitrogen source, bacteria can only grow when there is sufficient nickel in the fermentation broth to catalyze the urease enzyme's conversions of urea to ammonia and $CO_2$. Y easts use the urea amidolyase enzyme (which is not present in bacteria) to catalyze this conversion of urea to ammonia and $CO_2$. Urea amidolyase uses biotin instead of nickel as a catalyst. This difference between bacteria and yeasts is described in Strope, Pooja K., et al., "Molecular evolution of urea amidolyase and urea carboxylase in fungi", *BMC Evolutionary Biology* 11.1 (2011): 1-15, which is hereby incorporated by reference.

Monitoring the pH compared with the starting pH reveals that when the pH increases, the feed rate of urea is too high, and slowing the fed-batch rate of urea feeding will result in less ammonium being excreted. Bacteria can use ammonium as a nitrogen source, so when less or no ammonium is excreted, the ammonium is not available for the bacteria to consume.

A complication when limiting bacterial contamination by using urea as the main nitrogen source and limiting nickel, is that recycling yeast introduces between 10 and 50 mg/L of free amino nitrogen (FAN) to the fermentation broth due to yeast cell lysis. In addition, hydrolyzed grain, solutions from stalks of sugarcane and sweet sorghum, solutions from sugar beet juice, and solutions from sugar cane molasses and sugar beet molasses contain significant amounts of FAN, ranging from 50 mg/L to 400 mg/L of FAN.

If solutions containing FAN were fermented with urea as the nitrogen source, bacteria would grow faster on the FAN than yeast would grow on the combination of FAN and urea, because urea is preferred by yeast over some amino acids, resulting in significant growth of bacteria on the non-preferred amino acids.

In some variations, the invention solves this problem by adding recycled yeast in significantly larger concentrations than bacteria and letting the yeast initially grow using the FAN as the nitrogen source without addition of urea. For instance, if there is 250 mg/L of FAN in sweet sorghum juice and 50 mg/L of FAN from yeast cell lysis, and 100 g/L wet weight of recycled yeast is added to the sugar solution without adding urea, the recycled yeast will grow by about 10%, from 100 g/L to 110 g/L, depleting all the FAN in less than 30 minutes (15 minute lag time, 15 minute growth). The bacteria will also grow about 15% in this same time period but will stop growing when FAN is depleted. At this point, fed-batch addition of urea can start, and only yeast will grow without nickel in the fermentation broth and bacteria won't grow because FAN has been depleted. Note that recycled yeast will have a lag time of only about 15 minutes because it is typically already acclimated to the type of sugar solution being used and because no acid wash of the recycled yeast is performed. Approximately 90-95% of the yeast and 10-20% of the bacteria from the fermentation broth are recovered in the yeast cake by centrifugation. This 5× to 10× reduction in bacteria in the recycled yeast overcomes the 15% growth of bacteria on FAN, resulting in an equilibrium concentration of bacteria at the start of fermentation of about $10^5$ CFU/mL.

Grains that aren't malted but instead are hydrolyzed with alpha-amylase and glucoamylase enzymes usually produce between 50 mg/L and 100 mg/L of FAN because the protease enzymes from malting are what produce FAN in beer production. This is described in Peralta-Contreras, Mayeli, et al., "Fate of free amino nitrogen during liquefaction and yeast fermentation of maize and sorghums differing in endosperm texture", *Food and Bioproducts Processing* 91.1 (2013): 46-53, which is hereby incorporated by reference. Table 4 of this paper shows that liquefaction of 30% (w/v) mashes of ground corn and ground sorghum with alpha-amylase enzymes produced between 66 mg/L and 102 mg/L of FAN in the liquified mash.

The protein content per 100 g of grain is corn: 9.4 g; wheat: 12.6 g; rice: 7.1 g; and sorghum: 11.3 g. The FAN content of wheat in liquified mash is probably about 150 mg/L and the FAN content of rice in liquified mash is probably about 50 mg/L in the liquified mash.

Peralta-Contreras also shows in FIG. 1 that when yeast has a concentration of $10^7$ CFU/mL and the mash has a FAN concentration of 150 mg/mL, the yeast metabolizes all FAN in 27 hours during anaerobic fermentation. Since the concentration of yeast in this invention preferably has at least a wet weight of 50 g/L yeast (about $10^9$ CFU/mL), all FAN at 150 mg/L should be metabolized in 27/100 hours, or about 15 minutes. Similarly, all FAN at 300 mg/L should be metabolized by a wet weight of 100 g/L yeast in about 15 minutes.

The FAN content of sugarcane juice is described in Wang, Lu, et al., "Characterization and assessment of free amino acids in different varieties of sugarcane", *Industrial Crops and Products* 212 (2024): 118306, which is hereby incorporated by reference. Wang shows that the total free amino acid content of different varieties range from 51 mg/L to 782 mg/L. Converting this to mg/L of nitrogen, by multiplying by 0.15 gives a FAN content of 8 mg/L to 117.3 mg/L of nitrogen.

The FAN content of sugarcane juice is also described in Vidal, Esteban Espinosa, et al., "Influence of nitrogen supply on the production of higher alcohols/esters and expression of flavour-related genes in cachaça fermentation", *Food Chemistry* 138.1 (2013): 701-708, which is hereby incorporated by reference. Vidal states that the FAN content of sugarcane juice is about 100 mg/L of nitrogen.

The FAN content of sweet sorghum juice is described in Nasidi, Muhammad, et al., "Fermentation of stalk juices from different Nigerian sorghum cultivars to ethanol." *Bioethanol* 1.1 (2013), which is hereby incorporated by reference. Nasidi shows that the FAN content of different sweet sorghum cultivars in Nigeria ranges from 124 mg/L to 325 mg/L of nitrogen and that soil quality was the biggest factor.

The process for yeast recycling used widely in Brazil for fermenting sugarcane juice and sugarcane molasses is called the Melle-Boinot process, which was patented by Firmin Boinot in 1936 for fermenting sugar beet juice to ethanol. This is described by Boinot in U.S. Pat. No. 2,230,318, issued on Feb. 4, 1941, which is hereby incorporated by reference. The Melle-Boinot process involves separating yeasts and bacteria after fermentation using centrifugation, followed by a dilute sulfuric acid treatment which kills the bacteria without killing much of the yeast. However, this process is expensive, uses dangerous acids and causes problems with disposal of the effluent after treatment. By contrast, the present invention eliminates the need for acid treatment after separation of yeast, since the growth rate of bacteria is slowed by the techniques described above. A significant advantage of eliminating acid treatment of recycled yeast is that there is minimal cell lysis, resulting in less FAN from lysed yeast cells. The recycled yeast also has minimal lag time when restarting the next fermentation cycles, saving a few hours per fermentation cycle.

The yeast cream co-product is very valuable and can be used to make a single-cell protein product with about 50% protein. The yeast is alive and can also be used in baking and brewing. The yeast cream can be very cost-effectively dried, since after centrifugation it only has about 50% moisture. When the fermenter is aerated and when the yeasts don't exhibit the Crabtree effect, almost all sugar goes to yeast biomass, with a theoretical yield of about 0.50 g of dry matter per g of sugar. When yeasts are fermenting, there's an average yield of about 0.03 g of dry matter per g of sugar. *S. cerevisiae* exhibits the Crabtree effect, but *Candida utilis* does not, making *Candida utilis* ideal for producing single-cell protein.

When the yeast cream is to be used for human consumption, the RNA content needs to be reduced because excessive dietary RNA can lead to increased uric acid levels in the body, potentially causing health issues like gout or kidney stones. There are many methods for doing this, including enzymatic treatment, heat treatment, and autolysis.

In some embodiments, the sugar solution is produced from grain by first grinding the grain to produce a ground grain, forming a slurry of the ground grain and alpha-amylase enzymes and liquifying the slurry to a dextrin solution containing dextrin at a temperature above 80° C., saccharifying more than 95% of the dextrin to provide a saccharified solution using glucoamylase enzymes at a temperature between 50° C. and 65° C., and centrifuging the saccharified solution to produce a supernatant of the sugar solution and a co-product cake.

This is the first part of a common process used in production of glucose syrup using modern high-temperature alpha-amylase and glucoamylase enzymes. Since grain contains a significant amount of valuable protein, these proteins are recovered after saccharification with glucoamylase enzymes. The advantage of this method is that the glucoamylase has significantly higher activity at 65° C. than when using the Simultaneous Saccharification and Fermentation technique used worldwide in dry-grind corn ethanol plants, allowing fast saccharification that can performed at the same time as fermentation of a previous cycle, allowing the reduction of fermentation cycles from 48 hours to less than 12 hours. Separating the valuable protein-rich co-product before fermentation allows lower-cost separation of recycled yeast at the end of fermentation.

In some embodiments, the sugar solution is produced from solutions selected from the group consisting of sugarcane juice, clarified sugarcane juice, sugarcane molasses solution, raw sugar solution, sweet sorghum juice, clarified sweet sorghum juice, sugar beet juice, clarified sugar beet juice, sugar beet molasses solution, sucrose solution, glucose solution, fructose solution, mannose solution, galactose solution, lactose solution, xylose solution, maltose solution, and combinations thereof.

Using clarified juice removes impurities, reduces FAN and increases the speed for fermentation. Brazilian sugarcane ethanol plants use clarified sugarcane juice optionally mixed with some sugarcane molasses, showing the usefulness of this technique. In Brazil, sugarcane juice costs about the same amount of money per kg of sucrose as raw sugar, so a raw sugar solution is also cost-effective.

Since sugar solutions can be prepared from many types of feedstocks, an ethanol plant can use the same fermenters and distillation columns for different types of feedstocks, preparation of sugar solutions can operate in parallel with fermentation, and fermentation can operate in parallel with distillation. This also enables using the same fermentation tanks and distillation columns when a flex ethanol plant is able to processes both hydrolyzed grain and sugars from a variety of sources.

In some embodiments, the yeasts are selected from the group consisting of *Saccharomyces cerevisiae, Cyberlindnera jadinii, Kluyveromyces marxianus, Yarrowia lipolytica*, and combinations thereof. These four yeasts are Generally Recognized as Safe (GRAS) and can be used to produce ethanol from the sugar solutions or produce single-cell protein from the sugar solutions.

In some embodiments, the contaminating bacteria is *Lactobacillus fermentum*. Experience with Brazilian sugarcane ethanol plants and U.S. corn ethanol plants show that this is the most common contaminating bacteria, although other bacteria often contribute to bacterial contamination.

In some embodiments, the fermentation broth contains the ethanol which is separated, using distillation, to produce a hydrous ethanol product and distillation stillage.

Because yeast isn't washed with sulfuric acid before recycling, no calcium sulfate is in the distillation columns, which enables less cleaning of the distillation columns to remove deposits of calcium sulfate.

In some embodiments, the step of separating the recycled yeasts from the fermentation broth is selected from the group consisting of centrifugation, filtration, sedimentation, foam fractionation, and combinations thereof.

The most common way to separate recycled yeasts in Brazilian sugarcane ethanol plants is using a decanter centrifuge. These cost up to $1 million because of the high rate needed to maximize the production of a fermenter. A decanter centrifuge is a practical separation unit for this embodiment.

In some cases a belt filter is viable. While operational costs may be lower than centrifugation, the initial investment for a large-scale belt filter system (with sufficient capacity for 0.5-3 million liter fermenters) can be significant. Belt filters are not widely used in Brazilian sugarcane ethanol plants for yeast recycling, where centrifugation dominates due to its proven reliability and scalability.

When using recycled yeasts that sediment when sugars are depleted (yeasts with the NewFlo phenotype), these yeasts deposit rapidly in the bottom of the fermenter where they can be collected for recycling. This requires less capital and less operating costs than a decanter centrifuge, but may take longer. Foam fractionation might be appropriate for some yeasts, but isn't widely used.

In some embodiments, the co-product cake is dried to less than 12 wt % moisture to produce a dried animal feed product.

Bacteria, yeast, and fungi require more than 12 wt % moisture to grow, so drying is the most commonly used method for preventing spoilage of animal feed.

In some embodiments, a portion of the distillation stillage is mixed with water to form the slurry, and the remainder of the distillation stillage is concentrated to produce an animal feed syrup.

Distillation stillage from hydrolyzed grains often contains valuable protein that can be recovered by evaporation. The distillation stillage also contains glycerol, and organic acids and minerals such as phosphorus and other minerals, but only a part of this water can be re-used as process water in forming the slurry from ground grain to prevent buildup of these metabolites.

In a corn ethanol plant, approximately 50% of the distillation stillage (thin stillage) is typically recycled as "backset" to be mixed with ground corn and other recycled waters to create the slurry for the ethanol production process. The remaining thin stillage is sent to evaporators for condensing and mixing with products like dried distillers grains with solubles (DDGS). The exact percentage can vary depending on the plant's water balance and operational goals, with some facilities recycling between 20% to 80% of thin stillage, though 50% is a common average. In some embodiments, the grain is selected from the group consisting of corn, wheat, rice, sorghum, and combinations thereof. These are the most common grains used worldwide in dry-grind ethanol plants. All contain a significant amount of protein that is used to produce a valuable animal feed.

In some embodiments, the fermentation broth is in operable communication with a heat exchanger, wherein the heat exchanger is a plate heat exchanger comprising titanium heat exchange plates, and wherein the titanium heat exchange plates contain less than 1 g/kg nickel.

In some embodiments, the fermentation broth is in operable communication with a heat exchanger, and wherein the heat exchanger is a plate heat exchanger comprising stainless steel grade 316 heat exchange plates.

In some embodiments, the fermentation broth is in operable communication with a heat exchanger, wherein the heat exchanger is a spiral plate heat exchanger comprising titanium heat exchange plates, and wherein the titanium heat exchange plates contain less than 1 g/kg nickel.

In some embodiments, the fermentation broth is in operable communication with a heat exchanger, and wherein the heat exchanger is a spiral plate heat exchanger comprising stainless steel grade 316 heat exchange plates.

In acidic solutions containing chloride ions, stainless steel grade 304 leaches nickel into solution. One way to reduce the amount of nickel leached into the aqueous fermentation broth is to use heat exchangers made from titanium alloys with trace amounts of nickel, or grade 316 stainless steel. Nickel is a trace element in all titanium alloys except for the nitinol alloy, which has about 50% nickel and 50% titanium.

In some embodiments, the fermentation broth is cooled by evaporative cooling. In certain embodiments, the fermentation broth is sprayed into a space to form a spray, wherein air at less than 100% relative humidity is circulated through the space, wherein the air evaporates water from the spray, and wherein the spray is returned to the fermentation broth at a reduced temperature.

When growing yeast aerobically to produce single-cell protein, about 16 times more metabolic heat is produced by yeasts per kg of sugar compared to growing yeast anaerobically to produce ethanol. Using evaporative cooling using atmospheric air will remove metabolic heat from the fermenter while simultaneously oxygenating the fermenter. The added advantage is that there is no need for the fermentation broth to be recirculated through a heat exchanger that is 16 times larger than needed for anaerobic fermentation and less time is needed for disassembling and cleaning the heat exchanger.

In some embodiments, the ratio of the amount of the carbon source to the amount of the urea is selected such that essentially no urea remains in the fermentation broth before the hydrous ethanol product is separated from the fermentation broth by the distillation.

Ethyl carbamate, which is a known carcinogen, is produced by the reaction of urea and ethanol and elevated temperatures, and urea is safe in aerobic growth without ethanol production. U rea hydrogen peroxide does not produce ethyl carbamate unless ethanol is present at higher temperatures and therefore is safely used in tooth whiteners. Preferred variations of the present invention assure that no urea is present during distillation, which eliminates the problem of production of ethyl carbamate during distillation.

In some embodiments, the fermentation broth is oxygenated to maintain an oxygen level sufficient to support aerobic growth of the yeasts.

A preferred yeast that has been used to make single-cell protein for more than 80 years is *Cyberlindnera jadinii*, more commonly known as *Candida utilis* or Torula. It has been approved worldwide as a nutritional supplement for people and as an animal feed and fish feed. It is grown aerobically using sucrose, maltose, and a wide range of hexose sugars and pentose sugars.

In some embodiments, the fermentation broth is oxygenated using a method selected from the group consisting of air sparging, foam fermenting, mechanical agitation, and combinations thereof.

Persons skilled in the art will be familiar with using air sparging and mechanical agitation to oxygenate the fermentation broth.

Y easts can be grown with increased fatty acid amounts by growing with increased concentrations of sugar and yeast. Y east can be grown with increased concentrations of Omega-3 fatty acid (alpha-linolenic acid) content by growing with dissolved oxygen above 10 micromoles per liter. This is described in Babij, T., F. J. Moss, and B. J. Ralph., "Effects of oxygen and glucose levels on lipid composition of yeast *Candida utilis* grown in continuous culture", *Biotechnology and Bioengineering* 11.4 (1969): 593-603, which is hereby incorporated by reference. Increased lipid and Omega-3 content significantly increases the value of the yeast cream co-product.

Aerobic fermentation is used to grow microorganisms using oxygen dissolved in water and nutrients consisting of a carbon source, a nitrogen source, minerals and vitamins. These microorganisms are most commonly yeasts, fungi and bacteria. Fermentation is often used in the vernacular to mean anaerobic growth of yeast on sugar to produce ethanol, but aerobic fermentation specifically means aerobic growth of microorganisms with possible co-product production where respiration consumes $O_2$ and produces cell mass and $CO_2$.

Since oxygen is poorly soluble in water, solid-state fermentation is sometimes used, diffusing oxygen from air into a thin surface layer of water containing nutrients, causing microorganisms to grow aerobically. This has been used for millennia in Japan and other countries to ferment rice or soybeans using the fungus *Aspergillus oryzae*. However, it is difficult to do large-scale solid-state fermentation because a lot of surface area has to be produced between air and the damp substrate, and uniform removal of fermentation heat is costly and difficult. If the microorganism is a fungus, the mycelium of the fungus is easy to damage when using mixing to add air or remove heat.

Submerged fermentation of yeast is the most widely used aerobic fermentation technique, and generally introduces air bubbles at the bottom of a vessel which rise to the top of a vessel. The smaller the bubble, the higher the surface area-to-volume ratio and thus the more oxygen transfer to water. The air bubbles coalesce when they collide while rising, which significantly reduces the amount of oxygen transferred to the water. A lot of energy is used to introduce turbulence into the water to get bubbles to break up while rising. In addition, a lot of foam is produced because microorganisms secrete extracellular amphoteric proteins and polysaccharides which stabilize foam while growing aerobically. Conventionally, defoaming agents and foam breakers are used to break up foam before it overflows a fermenter. Submerged fermentation is capital-intensive per ton of microorganism produced because a stainless steel fermenter is needed to hold a lot of water, but only a few percent by dry weight of microorganisms can be produced in this water because of the poor solubility of oxygen in water. The cost of separation of microorganisms from water is very high because of this low concentration of microorganisms.

A foam fermenter uses a hybrid form of aerobic fermentation that combines some of the most useful features of solid-state fermentation and submerged fermentation.

A little-noticed foam fermenter was first described in 1937 by Hans Stöb in German Patent No. 681,847, which is hereby incorporated by reference. It describes making foam by sparging air into the bottom of a fermenter, forming a rising foam from these air-filled bubbles, fermenting microorganisms inside this foam, and then breaking this foam at the top of the fermenter using a spray of liquid from the bottom of the fermenter and recirculating the liquid from the foam.

The first practical foam fermenter was the Waldhof foam fermenter which was first described in 1940 by Walter Claus at Zellstofffabrik Waldhof in German Patent No. 759,121, which is hereby incorporated by reference. It was successfully used in Germany, expanding to produce 6,700 tons per year of *Candida utilis* from sulfite waste liquor in six sulfite pulp mills by 1944. The method described in this patent has several limitations, primarily the high energy consumption due to the spinning aerator/foam breaker, high capital costs and the inefficiency of cooling the fermentation media due to the insulating nature of foam.

In 1948 the Lake States Y east Corporation of Rhindlander, Wisconsin began using a Waldhof foam fermenter to grow *Candida utilis* on sulfite waste liquor. This is described in Inskeep, Gordon C., et al. "Food yeast from sulfite liquor", *Industrial & Engineering Chemistry* 43.8 (1951): 1702-1711, which is hereby incorporated by reference. A number of similar plants were built in the U.S. in the next few years.

A minor variation of the Waldhof foam fermenter is the Bartlesville foam fermenter, which was first described in 1976 by Donald Hitzman and Eugene Wegner at Phillips Petroleum Company, Bartlesville in U.S. Pat. No. 3,982,998, which is hereby incorporated by reference. The Bartlesville foam fermenter uses a spinning aerator at the bottom of a draft tube and a spinning mechanical foam breaker at the top of the fermenter. It suffers from the same weaknesses as the Waldhof foam fermenter-high energy consumption from the aerator and mechanical foam breaker, high capital costs and the inefficiency of cooling the fermentation media due to the insulating nature of foam.

By the end of the 1960s, most plants in the U.S. and Germany that were using Waldhof foam fermenters with sulfite waste liquor had been closed, since it was more economical to concentrate and burn the sulfite liquor solids than to lose money competing with soybean protein.

Similarly, the Bartlesville foam fermenters were never used to produce significant quantities of SCP from methanol (or any other substrate), because they produced protein that was uncompetitive with soybean protein, for the same technical reasons as the Waldhof foam fermenters.

Waldhof foam fermenters produced *Candida utilis* at a cell density of about 10 g on a dry matter basis, per kg of aqueous fermentation media (1%), but this low cell density was largely due to sulfite waste liquor containing only 1.5% sugars.

Bartlesville foam fermenters with 1.5 $m^3$ volume produced a biomass with a cell density of more than 110 g on a dry matter basis, per kg of aqueous fermentation media (11%). This is described in Shay, L. K., H. R. Hunt, and G. H. Wegner, "High-productivity fermentation process for cultivating industrial microorganisms", *Journal of industrial microbiology* 2.2 (1987): 79-85, which is hereby incorporated by reference. This paper claims that this higher cell density was achieved using the invention in U.S. Pat. No. 4,414,329 (increasing the concentration of mineral salts). Such high cell densities allowed drying without centrifugation and washing, which is much more economical than the process described by Inskeep.

Waldhof foam fermenters growing *Candida utilis* on sulfite waste liquor ran continuously for several years in open-top fermenters with no sterility control. Growing at a low pH with residual sulfite ($SO_2$) prevented competition by bacteria, and no competing yeasts or fungi were found to grow faster than *Candida utilis* on sulfite waste liquor.

The Waldhof foam fermenter described by Inskeep used an open-top vessel, 8 m in diameter (26 ft) and 4.2 m height (14 ft), which is a volume of about 210.5 $m^3$. The operating volume was about 204 $m^3$ of foam (45,000 gallons) or 91 $m^3$ (20,000 gallons) of liquor without air. The aerator/foam breaker was 1.2 m in diameter (4 ft) and was driven by a 186 KW (250 HP) motor which aerated the liquor at 2900 $m^3$/h (1700 $ft^3$/min). Inskeep states that the plant produced 4082 kg (4.5 tons, 9000 lbs) per day of dry yeast, which is 170 kg/h of dry yeast while using 186 kW of power, or 1.1 kWh/kg.

The Waldhof foam fermenter described by Inskeep used river water and a shell-and-tube heat exchanger to cool 6.8 $m^3$ (1500 gallons) of foam per minute. The heat generated by fermentation was 0.0044 kWh (3750 calories) per g of *Candida utilis*, or 4.4 kWh of heat per kg of *Candida utilis* produced. Using modern-day refrigeration with a Coefficient of Performance (COP) of 3.5 would require about 1.25 kWh electricity per kg of *Candida utilis* to remove 4.4 kWh of fermentation heat per kg of *Candida utilis.*

The Waldhof foam fermenter described by Inskeep operated with a productivity of 170 kg/91 $m^3$/h or 1.87 g/l/h. The Bartlesville foam fermenter described by Shay operated with a productivity of 25 g/l/h. This factor of 13 difference was due to the Bartlesville foam fermenter operating at 10 times the cell density of the Waldhof foam fermenter.

Shay showed that a foam fermenter can support yeast densities of 100 g/L dry weight. Brazilian sugarcane ethanol fermenters operate at 100 to 170 g/L wet weight, which is about 30 to 50 g/L dry weight. This shows that a foam fermenter can be used to support even higher yeast density than Brazilian sugarcane ethanol fermenters and can provide a very high oxygen transfer rate for rapid aerobic growth.

EXAMPLE

The following example demonstrates the principles of the disclosed invention. This invention, as described above, has been shown by experimental evidence to be useful for contamination control when growing yeasts.

In this example, two separate glass vessels with 400 mL of defined media were both inoculated with equal amounts of *Candida utilis* Y-264 and *Lactobacillus fermentum* B-8183. No stainless steel was in contact with either fermentation broth, and a ceramic bubbler was used to oxygenate the fermentation broth for 24 hours while the vessels were kept at 34° C. in a water bath. The carbon source in each vessel was 2.8 g of glucose and 0.05, 0.05, and 0.10 g urea was added to each vessel at the start of fermentation, after 4 hours, and after 8 hours, respectively. The defined media in both vessels comprised distilled water with 200 mg/L $KH_2PO_4$, 7 mg/L $ZnSO_4$, 4 mg/L $CuSO_4$, 20 mg/L $FeSO_4$, 5 mg/L M $nSO_4$, and 100 mg/L M $gSO_4$. Only one thing was different between the first and second vessel—the second vessel had 10 mg/L of $NiCl_2$ added.

After 24 hours of aerobic fermentation, the optical density of the first vessel increased from 0.132 to 2.025 and the optical density of the second vessel increased from 0.084 to 1.96. Previous tests showed that this fermentation entered stationary state (used up all the glucose) after 15 hours. Examination under a microscope showed that the first vessel (without added $NiCl_2$) contained mostly *Candida utilis* and the second vessel (with added $NiCl_2$) contained mostly *Lactobacillus fermentum.*

Other tests showed that adding all the urea at time 0 caused the pH of the solution to rise from about 6 to about 7, while adding the urea over time caused the pH to drop from about 5 to 4. This demonstrates that urea is preferably added at a rate that doesn't cause the pH to rise, since this is an indication that ammonia is being excreted by yeast (and bacteria can grow on ammonia).

This Example clearly demonstrates that when urea is the nitrogen source and when no sources of nickel are present during fermentation, *Candida utilis* (a yeast) grows faster than *Lactobacillus fermentum* (a bacteria), thereby preventing bacterial contamination.

In this detailed description, reference has been made to multiple embodiments and to the accompanying drawings in which are shown by way of illustration specific exemplary embodiments of the invention. These embodiments are described to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and figures described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims. In the case of conflict in definitions between the present disclosure and a dictionary or other reference, the present disclosure will be controlling.

I claim:

1. A method for contamination control when growing yeasts for a fermentation time, said method comprising:

(i) growing yeasts at a starting pH in a fermentation broth comprising a sugar solution, free amino nitrogen, a mineral source, yeasts, and contaminating bacteria without addition of urea, wherein said yeasts contain urea amidolyase enzymes, and said free amino nitrogen is an initial nitrogen source for growing said yeasts; and (ii) introducing said urea to said fermentation broth for growing said yeasts, wherein said urea is introduced to said fermentation broth via fed-batch feeding over time, with said fed-batch feeding commencing after said yeasts consume more than 90% of said free amino nitrogen in said fermentation broth, then controlling said fed-batch feeding such that the pH of said fermentation broth does not rise, due to addition of said urea, during the entirety of said fermentation time, wherein said urea is a primary nitrogen source for growing said yeasts after said yeasts consume more than 90% of said free amino nitrogen in said fermentation broth, wherein an amount of nickel in said fermentation broth is less than 1 mg nickel per kg of said fermentation broth during the entirety of said fermentation time, wherein said sugar solution contains sugars selected from the group consisting of sucrose, glucose, fructose, mannose, galactose, lactose, xylose, maltose, and combinations thereof, wherein said sugar solution has a starting concentration of greater than 50 g sugars per liter of said fermentation broth, wherein said free amino nitrogen has a starting concentration between 10 and 400 mg nitrogen per liter of said fermentation broth, wherein said yeasts have a starting concentration of more than 50 g yeasts per liter of said fermentation broth, on a wet weight basis, wherein said contaminating bacteria have a starting concentration of less than $10^7$ CFUs per milliliter of said fermentation broth, wherein said fermentation time is between 2 hours and 18 hours, during which said yeasts grow by metabolizing said sugars, said free amino nitrogen, said urea, and said mineral source in said fermentation broth, wherein said yeasts produce metabolites in said fermentation broth, and wherein said metabolites are selected from the group consisting of ethanol, carbon dioxide, glycerol, acetaldehyde, and combinations thereof, wherein a portion of said yeasts is separated from said fermentation broth after said fermentation time to produce recycled yeasts, wherein said recycled yeasts are not washed with acid, and wherein a fraction of said recycled yeasts is re-used in subsequent cycles as said yeasts, and a remaining fraction of said recycled yeasts is used as a yeast cream co-product.

2. The method of claim 1, wherein said sugar solution is produced from grain by first grinding said grain to produce a ground grain, forming a slurry of said ground grain and alpha-amylase enzymes and liquifying said slurry to a dextrin solution containing dextrin at a temperature above 80° C., saccharifying more than 95% of said dextrin to provide a saccharified solution using glucoamylase enzymes at a temperature between 50° C. and 65° C., and centrifuging said saccharified solution to produce a supernatant as said sugar solution and a co-product cake.

3. The method of claim 1, wherein said sugar solution is produced from a solution selected from the group consisting of sugarcane juice, clarified sugarcane juice, sugarcane molasses solution, raw sugar solution, sweet sorghum juice, clarified sweet sorghum juice, sugar beet juice, clarified sugar beet juice, sugar beet molasses solution, sucrose solution, glucose solution, fructose solution, mannose solution, galactose solution, lactose solution, xylose solution, maltose solution, and combinations thereof.

4. The method of claim 1, wherein said yeasts are selected from the group consisting of *Saccharomyces cerevisiae, Cyberlindnera jadinii, Kluyveromyces marxianus, Yarrowia lipolytica*, and combinations thereof.

5. The method of claim 1, wherein said contaminating bacteria are bacteria of *Lactobacillus fermentum.*

6. The method of claim 1, wherein said fermentation broth contains said ethanol which is separated, using distillation, to produce a hydrous ethanol product and distillation stillage.

7. The method of claim 1, wherein said recycled yeasts are separated from said fermentation broth by a process selected from the group consisting of centrifugation, filtration, sedimentation, foam fractionation, and combinations thereof.

8. The method of claim 2, wherein said co-product cake is dried to less than 12 wt % moisture to produce a dried animal feed product.

9. The method of claim 6, wherein a portion of said distillation stillage is mixed with water to form a slurry, and the remainder of said distillation stillage is concentrated to produce an animal feed syrup.

10. The method of claim 2, wherein said grain is selected from the group consisting of corn, wheat, rice, sorghum, and combinations thereof.

11. The method of claim 1, wherein said fermentation broth is in operable communication with a heat exchanger, wherein said heat exchanger is a plate heat exchanger comprising titanium heat exchange plates, and wherein said titanium heat exchange plates contain nickel at an amount of less than 1 g/kg.

12. The method of claim 1, wherein said fermentation broth is in operable communication with a heat exchanger, and wherein said heat exchanger is a plate heat exchanger comprising stainless steel grade 316 heat exchange plates.

13. The method of claim 1, wherein said fermentation broth is in operable communication with a heat exchanger, wherein said heat exchanger is a spiral plate heat exchanger comprising titanium heat exchange plates, and wherein said titanium heat exchange plates contain nickel at an amount of less than 1 g/kg.

14. The method of claim 1, wherein said fermentation broth is in operable communication with a heat exchanger, and wherein said heat exchanger is a spiral plate heat exchanger comprising stainless steel grade 316 heat exchange plates.

15. The method of claim 1, wherein said fermentation broth is cooled by evaporative cooling.

16. The method of claim 15, wherein said fermentation broth is sprayed into a space to form a spray, wherein air at less than 100% relative humidity is circulated through said space, wherein said air evaporates water from said spray, and wherein said spray is returned to said fermentation broth at a reduced temperature.

17. The method of claim 6, wherein a ratio of an amount of said sugar solution to an amount of said urea is selected such that essentially no urea remains in said fermentation broth before said hydrous ethanol product is separated from said fermentation broth by said distillation.

18. The method of claim 1, wherein said fermentation broth is oxygenated to maintain an oxygen level sufficient to support aerobic growth of said yeasts.

19. The method of claim 18, wherein said fermentation broth is oxygenated using a method selected from the group consisting of air sparging, foam fermenting, mechanical agitation, and combinations thereof.

* * * * *